(12) United States Patent
Elder et al.

(10) Patent No.: US 7,531,672 B2
(45) Date of Patent: May 12, 2009

(54) PREPARATION OF HETEROCYCLIC KETONES

(75) Inventors: Michael J. Elder, Rockville, MD (US); Robert L. Jones, Frankfurt (DE)

(73) Assignee: Basell Polyolefine GmbH, Wesseling (DE)

( * ) Notice: Subject to any disclaimer, the term of this patent is extended or adjusted under 35 U.S.C. 154(b) by 0 days.

(21) Appl. No.: 10/539,683

(22) PCT Filed: Dec. 17, 2003

(86) PCT No.: PCT/EP03/14358
§ 371 (c)(1),
(2), (4) Date: Nov. 9, 2006

(87) PCT Pub. No.: WO2004/056796
PCT Pub. Date: Jul. 8, 2004

(65) Prior Publication Data
US 2007/0142649 A1    Jun. 21, 2007

Related U.S. Application Data

(60) Provisional application No. 60/444,597, filed on Feb. 3, 2003.

(30) Foreign Application Priority Data
Dec. 19, 2002 (DE) .............................. 102 60 095

(51) Int. Cl.
*C07D 209/52* (2006.01)
*C07D 333/76* (2006.01)
(52) U.S. Cl. .......................... 548/516; 548/402; 549/51
(58) Field of Classification Search ................ 548/516; 549/51
See application file for complete search history.

(56) References Cited

FOREIGN PATENT DOCUMENTS

WO    WO-98/22486    5/1998

OTHER PUBLICATIONS

Ryabov, A. N. et al., "Zirconium Complexes with Cyclopentadienyl Ligands Involving Fused a Thiophene Fragment"Organometallics, 21, (2002), pp. 2842-2855.
Ewen, J. A. et al., "Chiral *Ansa* Metallocenes with Cp Ring-Fused to Thiophenes and Pyrroles: Syntheses, Crystal Structures, and Isotactic Polypropylene Catalysts", J. Am. Chem. Soc., 123, (2001), pp. 4763-4773.
Binder, D. et al., "A Facile Route to Functionalized Cyclopenta[*b*]thiophenones Based on the Structure of the Selective COX-2 Inhibitor Flosulide", Monatshefte für Chemie, 129, (1998), pp. 887-896.
Bergman, J. et al., "Intramolecular Ring Closure of α,β-Unsaturated 3-Acylindoles", Tetrahedron Letters, vol. 28, No. 32 (1987), pp. 3741-3744.
Beaton, C. M. et al., "Some Derivatives of 2- and 3-Phenylthiophen", J. C. S. Perkin I (1976), pp. 2355-2363.

*Primary Examiner*—Taofiq A Solola
(74) *Attorney, Agent, or Firm*—Jarrod N. Raphael

(57) ABSTRACT

The present invention relates to a process for preparing heterocyclic ketones of the formulae (I) and (Ia), by reacting a heterocyclic compound of the formula (II), with an α, β-unsaturated carboxylic acid of the formula (III), or with its anhydride of the formula (IV), where $R^1$ is hydrogen or a $C_1$-$C_{40}$ carbon-containing group, $R^2$ is hydrogen or a $C_1$-$C_{40}$ carbon-containing group, or $R^1$ and $R^2$ together form a cyclic ring system, $R^3$ is a $C_1$-$C_{40}$ carbon-containing group and X is an element of the 16th group of the Periodic Table or is a divalent nitrogen group —(N—$R^4$)—, where $R^4$ is an electron-withdrawing radical which is selected from the group consisting of perhalogenated $C_1$-$C_{40}$ carbon-containing radicals and $C_1$-$C_{40}$ organosulfonyl groups.

14 Claims, No Drawings

PREPARATION OF HETEROCYCLIC KETONES

RELATED APPLICATIONS

This application is a national stage application (under 35 U.S.C. 371) of PCT/EP2003/014358 filed Dec. 17, 2003 which claims benefit to German application 102 60 095.3 filed Dec. 19, 2002 and U.S. provisional application 60/444,597 filed Feb. 3, 2003.

The present invention relates to a process for preparing heterocyclic ketones of the formulae (I) and (Ia)

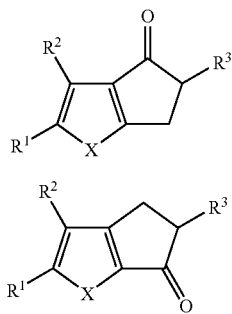

by reacting a heterocyclic compound of the formula (II)

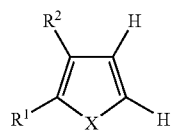

with an α,β-unsaturated carboxylic acid of the formula (III)

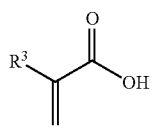

or with its anhydride of the formula (IV)

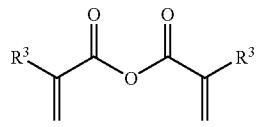

where
$R^1$ is hydrogen or a $C_1$-$C_{40}$ carbon-containing group,
$R^2$ is hydrogen or a $C_1$-$C_{40}$ carbon-containing group, or
$R^1$ and $R^2$ together-form a cyclic ring system,
$R^3$ is a $C_1$-$C_{40}$ carbon-containing group and
X is an element of the 16th group of the Periodic Table or is a divalent nitrogen group —(N—$R^4$)— where $R^4$ is an electron-withdrawing radical which is selected from the group consisting of perhalogenated $C_1$-$C_{40}$ carbon-containing radicals and $C_1$-$C_{40}$ organosulfonyl groups.

Substituted heterocyclic ketones are important starting products for preparing heterocyclic metallocene catalysts for the polymerization of α-olefins (J. Am. Chem. Soc., Vol. 123, No. 20, 4763-4773). Starting from substituted heterocyclic ketones, chiral heterocyclic ansa-metallocenes are obtainable which have a high significance as a transition metal component of highly active catalysts in stereo specific olefin polymerization (WO 98/22486).

Variation of the ligand system, for example by substitution, allows the catalyst properties of the metallocenes to be influenced in a targeted manner. This allows the polymer yield, the molecular weight distribution, the tactility and the melting point of the polymers to be varied to a desired extent, as is also observed in the case of the related ansa-bisindenylmetallocenes (Chem. Rev. 2000, No. 4).

Cyclopenta[b]thiophenes and cyclopenta[b]pyrroles are important ligand precursors for synthesizing the chiral heterocyclic ansa-metallocenes. Both cyclopenta[b]thiophenes and cyclopenta[b]pyrroles are generally prepared from the corresponding heterocyclic ketones. An example of a possibility of constructing a sulfur-containing cyclic ketosystem consists in the reaction of a substituted thiophene with methacrylic acid in the presence of super-polyphosphoric acid (J. Am. Chem. Soc., Vol. 123, No. 20, 4763-4773).

However, it was found that the reactions of methacrylic acid with 2-methylthiophene or with various 2,3-disubstituted thiophenes which bear bulky radicals did not lead to the corresponding heterocyclic ketones under the known reaction conditions in the presence of super-polyphosphoric acid, or the desired heterocyclic ketones were only obtained in unsatisfactory yields.

The synthesis of a substituted cyclopenta[b]benzothiophene by adding a benzothiophene to a mixture of a solution of phosphorous pentoxide in methanesulfonic acid and methacrylic acid at room temperature is also known (Organometallics, Vol. 21, No. 14, 2002, 2842-2855).

It is an object of the present invention to provide a simple, effective and economical process for preparing heterocyclic ketones which avoids the disadvantages of the known processes, and both makes novel heterocyclic ketones obtainable and allows the economical preparation of known representatives of the heterocyclic ketones.

We have found that this object is achieved by the process mentioned at the outset for preparing heterocyclic ketones of the formulae (I) or (Ia), which comprises performing the reaction in a liquid reaction medium which comprises at least one strong organic acid and at least one water absorbent, where the strong organic acid has a higher acid strength than the carboxylic acid of the formula (III), by adding simultaneously the heterocyclic compound of the formula (II) together with the α,β-unsaturated carboxylic acid of the formula (III) or together with its anhydride of the formula (IV) to said liquid reaction medium.

$R^1$ is hydrogen or a $C_1$-$C_{40}$ carbon-containing group, for example a $C_1$-$C_{40}$-alkyl radical, a $C_1$-$C_{10}$-fluoroalkyl radical, a $C_1$-$C_{12}$-alkoxy radical, a $C_6$-$C_{40}$-aryl radical, a $C_2$-$C_{40}$ heteroaromatic radical, a $C_6$-$C_{10}$-fluoroaryl radical, a $C_6$-$C_{10}$-aryloxy radical, a $C_3$-$C_{18}$-trialkylsilyl radical, a $C_2$-$C_{20}$-alkenyl radical, a $C_2$-$C_{20}$-alkynyl radical, a $C_7$-$C_{40}$-arylalkyl radical or a $C_8$-$C_{40}$-arylalkenyl radical. $R^1$ is preferably hydrogen, a cyclic, branched or unbranched $C_1$-$C_{20}$-, preferably $C_1$-$C_8$-alkyl radical, a $C_2$-$C_{12}$-, preferably $C_4$-$C_8$-ω-alkene-1-yl radical, a $C_6$-$C_{22}$-, preferably $C_6$-$C_{14}$-aryl radical or an arylalkyl radical having from 1 to 10, preferably from 1 to 4, carbon atoms in the alkyl radical and from 6 to 22, preferably from 6 to 10, carbon atoms in the aryl radical. Examples of particularly preferred $R^1$ radicals are methyl, ethyl, n-propyl, isopropyl, n-butyl, i-butyl, s-butyl, t-butyl, cyclopentyl, n-hexyl, cyclohexyl, 5-hexen-1-yl, 7-octen-1-yl, phenyl, 2-tolyl, 3-tolyl, 4-tolyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,5-di-(tert-butyl)-phenyl, 2,4,6-trimethylphenyl, 2,3,4-trimethylphenyl, 1-naphthyl, 2-naphthyl, phenanthryl, p-isopropylphenyl, p-tert-butylphenyl, p-s-butylphenyl, p-cyclohexylphenyl, p-trimethylsilylphenyl, benzyl or 2-phenylethyl, in particular methyl, i-propyl, 5-hexen-1-yl, phenyl, naphthyl, 2-3,5-di-(tert-butyl)-phenyl, p-tert-butylphenyl or benzyl.

$R^2$ is hydrogen or a $C_1$-$C_{40}$ carbon-containing group, for example a $C_1$-$C_{40}$-alkyl radical, a $C_1$-$C_{10}$-fluoroalkyl radical, a $C_1$-$C_{12}$-alkoxy radical, a $C_6$-$C_{40}$-aryl radical, a $C_2$-$C_{40}$ heteroaromatic radical, a $C_6$-$C_{10}$-fluoroaryl radical, a $C_6$-$C_{10}$-aryloxy radical, a $C_3$-$C_{18}$-trialkylsilyl radical, a $C_2$-$C_{20}$-alkenyl radical, a $C_2$-$C_{20}$-alkynyl radical, a $C_7$-$C_{40}$-arylalkyl radical or a $C_8$-$C_{40}$-arylalkenyl radical. $R^2$ is preferably hydrogen, a cyclic, branched or unbranched $C_1$-$C_{20}$-, preferably $C_1$-$C_8$-alkyl radical, a $C_6$-$C_{22}$-, preferably $C_6$-$C_{14}$-aryl radical or an arylalkyl radical having from 1 to 10, preferably from 1 to 4, carbon atoms in the alkyl radical and from 6 to 22, preferably from 6 to 10, carbon atoms in the aryl radical. Examples of particularly preferred $R^2$ radicals are hydrogen, methyl, ethyl, n-propyl, isopropyl, n-butyl, i-butyl, s-butyl, t-butyl, n-pentyl, cyclopentyl, n-hexyl, cyclohexyl, n-heptyl, n-octyl, phenyl, 2-tolyl, 3-tolyl, 4-tolyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,5-di-(tert-butyl)-phenyl, 2,4,6-trimethylphenyl, 2,3,4-trimethylphenyl, 1-naphthyl, 2-naphthyl, phenanthryl, p-isopropylphenyl, p-tert-butylphenyl, p-biphenyl, p-s-butylphenyl, p-cyclohexylphenyl, p-trimethylsilylphenyl, benzyl or 2-phenylethyl, in particular hydrogen, methyl, i-propyl, phenyl, naphthyl, 2-methylphenyl, 2,5-dimethylphenyl, 3,5-di-(tert-butyl)-phenyl, p-biphenyl, p-tert-butylphenyl or benzyl.

$R^1$ and $R^2$ together may also form a cyclic ring system which may be either monocycic or polycyclic and either saturated or unsaturated. The $R^1$ and $R^2$ radicals together are preferably a substituted or unsubstituted 1,3-butadiene-1,4-diyl group. The $R^1$ and $R^2$ radicals together are more preferably an unsubstituted 1,3-butadiene-1,4-diyl group or a singly or doubly terminally substituted 1,3-butadiene-1,4-diyl group where terminal substituents may have the same definition as $R^2$. Preferred terminal radicals on the 1,3-butadiene-1,4-diyl group are methyl or phenyl.

$R^3$ is a $C_1$-$C_{40}$ carbon-containing group, for example a $C_1$-$C_{40}$-alkyl radical, a $C_1$-$C_{10}$-fluoroalkyl radical, a $C_6$-$C_{40}$-aryl radical, a $C_2$-$C_{40}$ heteroaromatic radical, a $C_6$-$C_{10}$-fluoroaryl radical, a $C_7$-$C_{40}$-arylalkyl radical or a $C_3$-$C_{18}$-trialkylsilyl radical. $R^3$ is preferably a cyclic, branched or unbranched $C_1$-$C_{20}$-, preferably $C_1$-$C_8$-alkyl radical, a $C_6$-$C_{22}$-, preferably $C_6$-$C_{14}$-aryl radical, an arylalkyl radical having from 1 to 10, preferably from 1 to 4, carbon atoms in the alkyl radical and from 6 to 22, preferably from 6 to 10, carbon atoms in the aryl radical, or a $C_4$-$C_{24}$ heteroaromatic radical selected from the group consisting of substituted 2- or 3-thienyl radicals, substituted 2- or 3-furyl radicals or substituted pyrrole-2- or -3-yl radicals where the substituted five-membered heteroaromatic radicals bear no hydrogen atom in positions 2 and 5 and are identically or differently substituted in positions 1, 3 and 4 or are unsubstituted, and where the substituents on the five-membered heteroaromatic radicals are identical or different $C_1$-$C_{20}$ hydrocarbon radicals, for example $C_1$-$C_{20}$-, preferably $C_1$-$C_{40}$-alkyl radicals, or $C_6$-$C_{20}$-, preferably $C_6$-$C_{10}$-aryl radicals, in particular methyl, ethyl or phenyl. Examples of particularly preferred $R^3$ radicals include methyl, ethyl, isopropyl, t-butyl, cyclohexyl and phenyl, and $R^3$ is in particular methyl or phenyl.

X is an element of the 16th group of the Periodic Table, such as oxygen, sulfur, selenium or tellurium, preferably sulfur or selenium, in particular sulfur, or X is a divalent nitrogen group —(N—$R^4$)— where $R^4$ is an electron-withdrawing radical which is selected from the group consisting of perhalogenated $C_1$-$C_{40}$ carbon-containing radicals, for example a perfluorinated $C_1$-$C_{40}$-alkyl radical or perfluorinated $C_6$-$C_{22}$-aryl radical, or a $C_1$-$C_{40}$-organosulfonyl group, for example a $C_1$-$C_{20}$-alkylsulfonyl group or a $C_6$-$C_{14}$-arylsulfonyl group. Examples of preferred $R^4$ radicals include trifluoromethyl, n-nonafluorobutyl, pentafluorophenyl, heptafluoronaphthyl, methylsulfonyl, ethylsulfonyl, phenylsulfonyl, p-tolylsulfonyl or trifluoromethylsulfonyl. X is extremely preferably sulfur.

The term "alkyl" as used in the present context encompasses, unless further restricted, linear or singly or optionally also multiply branched saturated hydrocarbon radicals which may also be cyclic. Preference is given to $C_1$-$C_{18}$-alkyl, such as methyl, ethyl, n-propyl, n-butyl, n-pentyl, n-hexyl, n-heptyl, n-octyl, n-nonyl, n-decyl, cyclopentyl, cyclohexyl, isopropyl, isobutyl, isopentyl, isohexyl, sec-butyl or tert-butyl.

The term "alkenyl" as used in the present context encompasses linear or singly or optionally also multiply branched hydrocarbon radicals having at least one, optionally also more than one, C—C double bonds which may be cumulated or conjugated. Preference is given to $C_2$-$C_{12}$-ω-alken-1-yl radicals such as vinyl, allyl, 3-buten-1-yl, 5-hexen-1-yl, 7-octen-1-yl and 9-decen-1-yl.

The term "aryl" as used in the present context refers, unless further restricted, to aromatic and optionally also fused polyaromatic hydrocarbon radicals which may optionally be mono- or polysubstituted by linear or branched $C_1$-$C_{18}$-alkyl, $C_1$-$C_{18}$-alkoxy, $C_2$-$C_{10}$-alkenyl or $C_3$-$C_{15}$-alkylalkenyl. Preferred examples of substituted and unsubstituted aryl radicals are in particular phenyl, 2-methylphenyl, 4-methylphenyl, 4-ethylphenyl, 4-propylphenyl, 4-isopropylphenyl, 4-tert-butylphenyl, 4-methoxyphenyl, 1-naphthyl, 9-anthryl, 9-phenanthryl, 3,5-dimethylphenyl, 3,5-di-tert-butylphenyl or 4-trifluoromethylphenyl.

The term "heteroaromatic radical" as used in the present context refers to aromatic hydrocarbon radicals in which one or more carbon atoms are replaced by nitrogen, phosphorus, oxygen or sulfur atoms or combinations thereof. These may optionally be mono- or polysubstituted by linear or branched $C_1$-$C_{18}$-alkyl, $C_2$-$C_{10}$-alkenyl or $C_6$-$C_{10}$-aryl. Preferred examples include thienyl, furyl, pyrrolyl, pyridyl, pyrazolyl, imidazolyl, oxazolyl, thiazolyl, pyrimidinyl, pyrazinyl and the like, and also methyl, ethyl, propyl, isopropyl and tert-butyl radical-substituted derivatives thereof.

For the process according to the invention, particular preference is given to $R^3$ being methyl and X being sulfur and $R^1$ and $R^2$ each being as defined above.

The process according to the invention is notable in that the reaction is performed in a liquid reaction medium which comprises at least one strong organic acid and at least one water absorbent, where the strong organic acid has a higher acid strength than the carboxylic acid of the formula (III), by adding simultaneously the heterocyclic compound of the formula (II) together with the α,β-unsaturated carboxylic acid of the formula (III) or together with its anhydride of the formula (IV) to said liquid reaction medium. Preference is given to adding a preformed mixture of the reaction components to the liquid reaction medium.

The strong organic acids which may be used in the process according to the invention have a higher acid strength than the carboxylic acids of the formula (III). Examples of preferred strong organic acids include perhalogenated carboxylic acids, for example trichloroacetic acid, trifluoroacetic acid or perfluoropropionic acid, or $C_1$-$C_{18}$-alkylsulfonic acids which may also be halogenated. Preference is given to using $C_1$-$C_8$-, in particular $C_1$-$C_4$-alkylsulfonic acids in the process according to the invention. Preferred examples are methanesulfonic acid, trifluoromethanesulfonic acid and ethanesulfonic acid, in particular methanesulfonic acid.

The water absorbent should be capable of binding water of reaction in the acid reaction medium physically, for example in the case of a molecular sieve, or chemically, for example in the case of phosphorus pentoxide. Preference is given to using phosphorus pentoxide as the water absorbent in the process according to the invention.

In addition to the strong organic acid and the water-absorbent drying agent, the liquid reaction medium may also comprise inert solvents, for example alkanes or halogenated alkanes. Examples of suitable alkanes include pentane, hexane, heptane and dodecane, and examples of suitable halogenated alkanes include methylene chloride and 1,2-dichloroethane.

Preference is given to performing the process according to the invention in a liquid reaction medium which consists of more than 50% by weight of a mixture of methanesulfonic acid and phosphorus pentoxide. Very particular preference is given to the liquid reaction medium consisting of more than 90% by weight of a mixture of methanesulfonic acid and phosphorus pentoxide. The starting compounds of the formulae (II), (III) and (IV) are not to be regarded as components of the above-described liquid reaction medium.

In the process according to the invention, the molar ratio of the heterocyclic compound of the formula (II) to the α,β-unsaturated carboxylic acid of the formula (III) is typically in the range from 5:1 to 1:100. Preference is given to the ratio being in the range from 2:1 to 1:3, in particular in the range from 1.1:1 to 1:1.5. When the anhydride of the formula (IV) is used instead of the α,β-unsaturated carboxylic acid of the formula (III), it should be noted that one mole of anhydride of the formula (IV) corresponds to two moles of carboxylic acid of the formula (III) in the process according to the invention:

The mass ratio of the heterocyclic compound of the formula (II) to the liquid reaction medium in the process according to the invention is typically in the range from 1:2 to 1:1000, preferably in the range from 1:3 to 1:50, more preferably in the range from 1:5 to 1:35.

In the process according to the invention, the mass ratio of the water absorbent to the strong organic acid is preferably in the range from 1:99 to 25:75. In the case of phosphorus pentoxide and methanesulfonic acid, the mass ratio is in particular between 5:95. and 15:85.

The reaction temperature in the process according to the invention is typically in the range from 20 to 200° C., preferably in the range from 50 to 110° C., in particular in the range from 60 to 90° C. At a reaction temperature of 20° C., a very low conversion was observed, at only 60° C. a satisfactory conversion and, at 110° C., the maximum of the conversion to the desired reaction product was exceeded.

The process according to the invention is typically carried out under atmospheric pressure. However, it may in principle also be carried out under reduced or elevated pressure. It is important merely that the reaction partners are present together in the liquid reaction medium under the reaction conditions, in order to be able to-react with each other in an optimum manner.

The starting compounds of the formulae (II), (III) and (IV) are known and commercially obtainable, or can be prepared by literature processes. For example, 2,3-disubstituted thiophenes can be prepared as described in J. Chem. Soc., Perkin 1, 22, (1976), pages 2355-2363.

The process according to the invention is notable for good yields, high space-time yields and simple isolation and workup of the reaction products from the reaction mixture.

The invention is illustrated by the following, nonlimiting examples:

EXAMPLES

General Information:

Mass spectra were measured using a Hewlett Packard 6890 instrument which was equipped with a 5973 mass analyzer (EI, 70 eV).

Super-PPA (super-polyphosphoric acid) was prepared typically by completely dissolving 164.3 g of phosphorus pentoxide in 975.7 g of commercially obtainable polyphosphoric acid (Aldrich) at 140° C. with stirring.

Eaton's reagent was used as commercially obtained (Aldrich; 7.5% by weight of phosphorus pentoxide in methanesulfonic acid).

Example 1

Synthesis of 2,5-dimethyl-4,5-dihydrocyclopenta[b]thiophen-6-one

A mixture of 150 g of 2-methylthiophene (1.5 mol) and 157.5 g of methacrylic acid (1.8 mol) was added within 30 minutes at about 80° C. to 1500 ml of Eaton's reagent, and the temperature was between 78° C. and 83° C. On completion of addition, the reaction mixture was stirred for a further 5 minutes and then gradually poured into a vigorously stirred mixture of 3000 ml of water and 500 ml of dichloromethane. The organic phase was removed and dried over magnesium sulfate. The solvent was distilled off on a rotary evaporator and 263.5 g of crude product were obtained in a purity of 88.2% according to GC-MS analysis. A portion of the crude product (79 g) was distilled (92° C., 0.02 torr). 56.5 g (76%) of product were obtained as a mixture of two isomers in a ratio of approx. 9:1 (thiophen-6-one: thiophen-4-one).

$^1$H NMR of the main isomer (CDCl$_3$): δ 6.8 (s, 1H), 3.2 (dd, 1H), 2.95 (m, 1H), 2.5 (s, 3H), 2.4 (m, 1H), 1.25 (d, 3H); EI/MS: m/z (%) 165 ([M$^+$], 72), 151 (100), 123 (23), 97 (11), 69 (15).

Comparative Example A

Synthesis of 2,5-dimethyl-4,5-dihydrocyclopenta[b]thiophen-6-one

A solution of 100 g of 2-methylthiophene (1.02 mol) and 104 ml of methacrylic acid (1.22 mol) in 200 ml of dichloromethane was added dropwise within 30 minutes at 80° C. to 1000 g of super-PPA. Afterwards, the reaction mixture was stirred at 80° C. for 3 hours. The dark red mixture was poured into 1000 g of crushed ice and stirred until the polyphosphoric acid had completely dissolved. The aqueous phase was extracted twice with 400 ml each time of a dichloromethane/hexane solvent mixture (30 parts by volume/70 parts by volume). The combined organic phases were washed with a saturated aqueous solution of sodium hydrogencarbonate and dried over magnesium sulfate. After removal of the solvents on a rotary evaporator, 136 g of crude product were obtained. The distillation of the crude product (90° C., 0.1 torr) gave 76 g (46%) of product.

Example 2

Synthesis of 2,5-dimethyl-3-naphthalen-1-yl-4,5-dihydrocyclopenta[b]thiophen-6-one (2)

A mixture of 5 g of 2-methyl-3-naphthalen-1-ylthiophene (0.022 mol) and 2.1 ml of methacrylic acid (0.025 mol) was added within 15 minutes at 80° C. to 125 ml of Eaton's reagent. After a further 5 minutes, the reaction mixture was poured into ice-water and the precipitated product was dissolved by adding 300 ml of dichloromethane. The organic phase was removed, washed with a saturated aqueous solution of sodium hydrogencarbonate and dried over magnesium sulfate. After removing the solvent, 5 g of product (2) were obtained which, according to GC analysis, was present as a single isomer in 99% purity.

$^1$H NMR (CDCl$_3$): δ 7.8-8.0 (t, 2H), 7.3-7.6 (m, 5H), 2.8-3.0 (m, 2H), 2.2-2.4 (m, 1H), 2.3 (s, 3H), 1.25 (d, 3H); EIMS: m/z (%) 292 ([M$^+$], 100), 277 (62), 263 (15), 249 (16), 235 (15), 215 (8), 202 (9), 189 (6), 165 (9).

Comparative Example B

Attempt to synthesize 2,5-dimethyl-3-naphthalen-1-yl-4,5-dihydrocyclopenta[b]thiophen-6-one (2)

A solution of 5 g of 2-methyl-3-naphthalen-1-ylthiophene (0.022 mol) and 2.5 ml of methacrylic acid (0.03 mol) in 60 ml of dichloromethane was added at 70° C. to 300 g of super-PPA and stirred for 20 h. GC-MS analysis of the reaction mixture showed only starting product and no product (2) at all.

Example 3

Synthesis of 5-methyl-2-phenyl-3-o-tolyl-4,5-dihydrocyclopenta[b]thiophen-6-one (3)

A mixture of 31.8 g of 2-phenyl-3-o-tolyl-thiophene (0.127 mol) and 13.3 ml of methacrylic acid (0.157 mol) was added within 30 minutes at about 80° C. to 500 ml of Eaton's reagent. On completion of the addition, the reaction mixture was stirred for a further 5 minutes and then gradually added to crushed ice. 300 ml of dichloromethane were added to dissolve the reaction product. The organic phase was removed, washed with a saturated aqueous solution of sodium hydrogencarbonate and dried over magnesium sulfate. After removing the solvent, 39 g of product (3) were obtained which, according to GC-MS, constituted a single, isomer and had a purity of 95%.

$^1$H NMR (CDCl$_3$): δ 7.0-7.3 (m, 4H), 2.8-3.1 (m, 2H), 2.2-2.4 (m, 1H), 1.9 (s, 3H), 125 (dd, 3H); EIMS: m/z (%) 318 ([M$^+$], 100), 303 (39), 275 (16), 261 (11), 247 (6), 228 (8), 215 (13), 202 (6), 189 (6), 165 (6).

Comparative Example C

Attempt to synthesize 5-methyl-2-phenyl-3-o-tolyl4,5-dihydrocyclopenta[b]thiophen-6-one (3)

A mixture of 5 g of 2-phenyl-3-o-tolylthiophene (0.02 mol) and 2.5 ml of methacrylic acid (0.03 mol) was added to 75 g of super-PPA at 90° C. and stirred for 5 hours. In addition to starting product, GC-MS analysis of the reaction mixture showed less than 5% of product (3).

Example 4

Synthesis of 2-methyl-1,2-dihydrobenzo[b]cyclopenta[d]thiophen-3-one

A mixture of 13.4 g of benzo[b]thiophene (0.10 mol) and 9.04 g of methacrylic acid (0.105 mol) was added at 65° C. to 134 g of Eaton's reagent The reaction mixture was stirred at 65° C. for 1 hour and then poured into 150 ml of water. The aqueous phase was extracted using a dichloromethane/hexane solvent mixture (30 parts by volume/70 parts by volume). The combined organic phases were washed with water and dried over magnesium sulfate. After removing the solvents under reduced pressure, 14.7 g (72.8%) of product were obtained which, according to GC, contained two isomers in a ratio of approx. 3:1 (thiophen-3-one:thiophen-1-one).

EIMS of M$^+$ for C$_{12}$H$_{10}$OS:202.0 (observed), 202.27 (calculated).

Comparative Example D

Synthesis of 2-methyl-1,2-dihydrobenzo[b]cyclopenta[d]thiophen-3-one

A solution of 66.9 g of benzo[b]thiophene (0.5 mol) and 46.3 g of methacrylic acid (0.537 mol) in 60 ml of dichloromethane was added dropwise starting at 70° C. within 20 minutes to 1000 g of super-PPA. The temperature was maintained at 65-70° C. during the addition. Methylene chloride was distilled off. After 2 h of reaction time, the reaction mixture was poured onto crushed ice and stirred until the polyphosphoric acid had completely dissolved. The aqueous phase was extracted with a dichloromethane/hexane solvent mixture (30 parts by volume/70 parts by volume). The combined organic phases were washed with a saturated aqueous solution of sodium hydrogen-carbonate and with water and dried over magnesium sulfate. After removing the solvents under reduced pressure, 79.8 g of a dark orange oil (71%) were obtained.

$^1$H NMR, 2 isomers (CD$_2$Cl$_2$): δ 7.2-8.2 (m, 4H), 2.6-3.4 (m, 3H), 1.3 (m, 3H).

Example 5

Synthesis of 2-methyl-8-phenyl-1,2-dihydrobenzo[b]cyclopenta[d]thiophen-3-one

A mixture of 10 g of 4-phenylbenzo[b]thiophene (47.6 mmol) and 4.8 ml of methacrylic acid (56.6 mmol) was added within 30 minutes to 100 ml of Eaton's reagent at a reaction temperature during the addition of 80° C. The reaction mixture was cooled to 60° C. and gradually stirred into 400 ml of water with vigorous stirring. The addition of 250 ml of dichloromethane dissolved the precipitated product. After phase separation, the organic phase was washed with a saturated solution of sodium hydrogencarbonate and with water, and then dried over magnesium sulfate.

The solvent was removed and 12 g of product were obtained. According to GC, the product had a purity of 90% and consisted of two isomers which were present in a ratio of about 7:3 (thiophen-3- one: thiophen-1-one).

$^1$H NMR of the main isomer (CDCl$_3$): δ 7.8 (d, 1H), 7.2-7.5 (m, 7H), 2.85 (m,1H), 2.7 (d. 1H), 2.05 (d, 1H), 1.1 (d, 3H);

EIMS: m/z (%) 278 ([M⁺], 100), 263 (65), 249 (13), 234 (21), 221 (47), 202 (16), 189 (9), 176 (6), 163 (8), 151 (3), 139 (3).

Comparative Example E

Attempt to Synthesize 2-methyl-8-phenyl-1,2-dihydrobenzo[b]cyclopenta[d]thiophen-3-one A solution of 76.2 g of 4-phenylbenzo[b]thiophene (0.36 mol) and 37.5 ml of methacrylic acid (0.44 mol) in 50 ml of dichloromethane was added dropwise to 1000 g of super-PPA heated to 80° C. and stirred at 80° C. for 5 hours. The dark red mixture was added to 1000 g of crushed ice and stirred until the polyphosphoric acid had completely dissolved. The aqueous phase was extracted twice with 400 ml each time of a dichloromethane/hexane solvent mixture (30/70 parts by volume). The GC-MS. of the organic phase showed only starting product and no trace of the desired product.

Table 1 shows a comparison of examples 1 to 5 and comparative examples A to E

TABLE 1

| | Reaction$^{a)}$ | Reaction time [h] | Yield [%] |
|---|---|---|---|
| Example 1 Comparative example A | | 0.25 3.0 | 76 46 |
| Example 2 Comparative example B | | 0.25 20 | 81 none |
| Example 3 Comparative example C | | 0.25 4.5 | 86 <5 |

TABLE 1-continued

| Example | Reaction[a] | Reaction time [h] | Yield [%] |
|---|---|---|---|
| Example 4 Comparative example D | [benzothiophene] + [methacrylic acid] → [product] | 1.0 2.0 | 73 71 |
| Example 5 Comparative example E | [4-phenylbenzothiophene] + [methacrylic acid] → [product] | 0.5 5.0 | 90 none |

[a]only the main isomer is illustrated

Example 6

Attempts to Synthesize 2,5-dimethyl-4,5-dihydrocyclopenta[b]thiophen-6-one

In table 2, various experiments are compiled which were carried out in a similar manner to example 1, and the mass ratio of 2-methylthiophene to Eaton's reagent and the reaction temperature were varied.

TABLE 2

| | Mass ratio of Eaton's reagent/ 2-methylthiophene | Reaction temperature [° C.] | Yield* [%] |
|---|---|---|---|
| Example 6a | 28 | 20 | <5 |
| Example 6b | 28 | 80 | 88 |
| Example 6c | 28 | 70 | 91 |
| Example 6d | 28 | 60 | 67 |
| Example 6e | 14 | 80 | 97 |
| Example 6f | 6 | 80[a] | 53 |

[a]during the addition, the temperature rose to 110° C. owing to the exothermic reaction and the high concentration of the reaction partners
*yields were only determined by means of GC analyses

We claim:

1. A process for preparing heterocyclic ketones of the formulae (I) or (Ia)

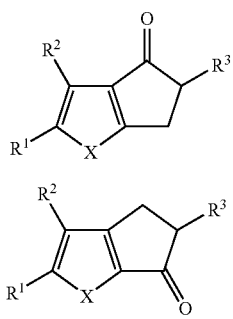

by reacting a heterocyclic compound of the formula (II)

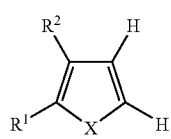

with an α,β-unsaturated carboxylic acid of the formula (III)

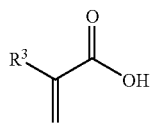

(III)

or with its anhydride of the formula (IV)

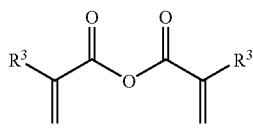

(IV)

which comprises performing the reaction in a liquid reaction medium which comprises at least one strong organic acid and at least one water absorbent, where the strong organic acid has a higher acid strength than the carboxylic acid of the formula (III) by adding simultaneously the heterocyclic compound of the formula (II) together with the α,β-unsaturated carboxylic acid of the formula (III) or together with its anhydride of the formula (IV) to said liquid reaction medium, and wherein the reaction is carried out in the temperature range from 60 to 90° C., and
where
$R^1$ is hydrogen or a $C_1$-$C_{40}$-alkyl radical, a $C_1$-$C_{10}$-fluoroalkyl radical, a $C_1$-$C_{12}$-alkoxy radical, a $C_6$-$C_{40}$-aryl radical, a $C_2$-$C_{40}$ heteroaromatic radical, a $C_6$-$C_{10}$-fluoroaryl radical, a $C_6C_{10}$-aryloxy radical, a $C_3$-$C_{18}$-trialkylsilyl radical, a $C_2$-$C_{20}$-alkenyl radical, a $C_2$-$C_{20}$-alkynyl radical, a $C_7$-$C_{40}$-arylalkyl radical or a $C_8$-$C_{40}$-arylalkenyl radical,
$R^2$ is hydrogen or a $C_1$-$C_{40}$-alkyl radical, a $C_1$-$C_{10}$-fluoroalkyl radical, a $C_1$-$C_{12}$-alkoxy radical, a $C_6$-$C_{40}$-aryl radical, a $C_2$-$C_{40}$ heteroaromatic radical, a $C_6$-$C_{10}$-fluoroaryl radical, a $C_6$-$C_{10}$-aryloxy radical, a $C_3$-$C_{18}$-trialkylsilyl radical, a $C_2$-$C_{20}$-alkenyl radical, a $C_2$-$C_{20}$-alkynyl radical, a $C_7$-$C_{40}$-arylalkyl radical or a $C_8$-$C_{40}$-arylalkenyl radical, or
$R^1$ and $R^2$ together form a cyclic ring system,
$R^3$ is a $C_1$-$C_{40}$-alkyl radical, a $C_1$-$C_{10}$-fluoroalkyl radical, a $C_6$-$C_{40}$-aryl radical, a $C_2$-$C_{40}$ heteroaromatic radical, a $C_6$-$C_{10}$-fluoroaryl radical, a $C_7$-$C_{40}$-arylalkyl radical or a $C_3$-$C_{18}$-trialkylsilyl radical, and
X is an element of the 16th group of the Periodic Table or is a divalent nitrogen group —(N—$R^4$)—, where $R^4$ is an electron-withdrawing radical which is selected from the group consisting of perhalogenated $C_1$-$C_{40}$ carbon-containing radicals and $C_1$-$C_{40}$ organosulfonyl groups.

2. A process as claimed in claim 1, wherein X is sulfur.

3. A process as claimed in claim 1, wherein the strong organic acid is a $C_1$-$C_8$-alkylsulfonic acid.

4. A process as claimed in claim 1, wherein the water absorbent is phosphorus pentoxide.

5. A process as claimed in claim 1, wherein at least 50% by weight of the liquid reaction medium is a mixture of methanesulfonic acid and phosphorus pentoxide.

6. A process as claimed in claim 1, wherein the molar ratio of the heterocyclic compound of the formula (II) to the α,β-unsaturated carboxylic acid of the formula (III) is in the range from 5:1 to 1:100.

7. A process as claimed in claim 1, wherein the mass ratio of the heterocyclic compound of the formula (II) to the liquid reaction medium is in the range from 1:2 to 1:1000.

8. A process as claimed in claim 1, wherein the mass ratio of the water absorbent to the strong organic acid is in the range from 1:99 to 25:75.

9. A process as claimed in claim 2, wherein the strong organic acid is a $C_1$-$C_8$-alkylsulfonic acid.

10. A process as claimed in claim 9, wherein the water absorbent is phosphorus pentoxide.

11. A process as claimed in claim 10, wherein at least 50% by weight of the liquid reaction medium is a mixture of methanesulfonic acid and phosphorus pentoxide.

12. A process as claimed in claim 11, wherein the molar ratio of the heterocyclic compound of the formula (II) to the α,β-unsaturated carboxylic acid of the formula (III) is in the range from 5:1 to 1:100.

13. A process as claimed in claim 12, wherein the mass ratio of the heterocyclic compound of the formula (II) to the liquid reaction medium is in the range from 1:2 to 1:1000.

14. A process as claimed in claim 13, wherein the mass ratio of the water absorbent to the strong organic acid is in the range from 1:99 to 25:75.

* * * * *